(12) United States Patent
Lau

(10) Patent No.: US 11,975,166 B2
(45) Date of Patent: May 7, 2024

(54) COMFORTABLE MEDICAL CONNECTORS

(71) Applicant: CareFusion 303, Inc., San Diego, CA (US)

(72) Inventor: Choi Ting Lau, Santee, CA (US)

(73) Assignee: CAREFUSION 303, INC., San Diego, CA (US)

( * ) Notice: Subject to any disclaimer, the term of this patent is extended or adjusted under 35 U.S.C. 154(b) by 303 days.

(21) Appl. No.: 17/037,461

(22) Filed: Sep. 29, 2020

(65) Prior Publication Data

US 2022/0096807 A1 Mar. 31, 2022

(51) Int. Cl.
*A61M 39/02* (2006.01)

(52) U.S. Cl.
CPC . *A61M 39/0247* (2013.01); *A61M 2039/0202* (2013.01); *A61M 2039/0205* (2013.01); *A61M 2039/0282* (2013.01); *A61M 2039/0288* (2013.01); *A61M 2205/0211* (2013.01); *A61M 2205/0216* (2013.01); *A61M 2205/0238* (2013.01); *A61M 2205/584* (2013.01)

(58) Field of Classification Search
CPC ...... A61M 39/0247; A61M 2039/0202; A61M 2039/0205; A61M 2039/0282; A61M 2039/0288; A61M 2205/0211; A61M 2205/0216; A61M 2205/0238; A61M 2205/584; A61M 39/10; A61M 39/12; A61M 39/0208; A61M 25/0637; A61M 5/158
See application file for complete search history.

(56) References Cited

U.S. PATENT DOCUMENTS

| | | | | |
|---|---|---|---|---|
| 2,847,995 A | * | 8/1958 | Adams | A61M 5/162 604/905 |
| 3,900,184 A | | 8/1975 | Burke et al. | |
| 4,710,174 A | * | 12/1987 | Moden | A61M 39/0208 604/244 |
| 4,781,680 A | * | 11/1988 | Redmond | A61M 39/0208 604/86 |
| 5,013,298 A | * | 5/1991 | Moden | A61M 39/0208 604/86 |
| 5,509,409 A | * | 4/1996 | Weatherholt | A61M 25/02 128/207.18 |

(Continued)

FOREIGN PATENT DOCUMENTS

| EP | 3220972 A1 | 9/2017 |
|---|---|---|
| EP | 3368120 A1 | 9/2018 |

OTHER PUBLICATIONS

International Search Report and Written Opinion for Application No. PCT/US2021/052083, dated Jan. 28, 2022, 15 pages.

(Continued)

*Primary Examiner* — Theodore J Stigell
(74) *Attorney, Agent, or Firm* — Morgan, Lewis & Bockius LLP

(57) ABSTRACT

A medical connector for minimizing discomfort to a patient may include a substantially rigid inner body and a flexible outer body having a patient interfacing surface and coupled to at least a portion of the substantially rigid inner body. The patient interfacing surface may include a cushion material. The cushion material may be interposed between the substantially rigid inner body and the patient's skin when the medical connector is attached to the patient.

18 Claims, 3 Drawing Sheets

(56) References Cited

U.S. PATENT DOCUMENTS

| | | | | |
|---|---|---|---|---|
| 8,821,373 B2* | 9/2014 | Schwab | ............ | A61M 39/0208 606/157 |
| 2004/0068233 A1* | 4/2004 | DiMatteo | .......... | A61M 39/0208 604/177 |
| 2004/0243103 A1* | 12/2004 | King | ................ | A61M 25/0009 604/533 |
| 2006/0015086 A1* | 1/2006 | Rasmussen | ....... | A61M 25/0097 604/533 |
| 2008/0281297 A1* | 11/2008 | Pesach | ................ | A61M 5/1723 604/113 |
| 2009/0069792 A1* | 3/2009 | Frey | ................ | A61M 25/0009 264/261 |
| 2013/0012870 A1 | 1/2013 | Dikeman et al. | | |

OTHER PUBLICATIONS

3M, "Tegaderm™ I.V. Advanced Securement Dressings Product Information", 3M Critical & Chronic Care Solutions Division 3M Health Care, 2011, 2014, 5 pages.

* cited by examiner

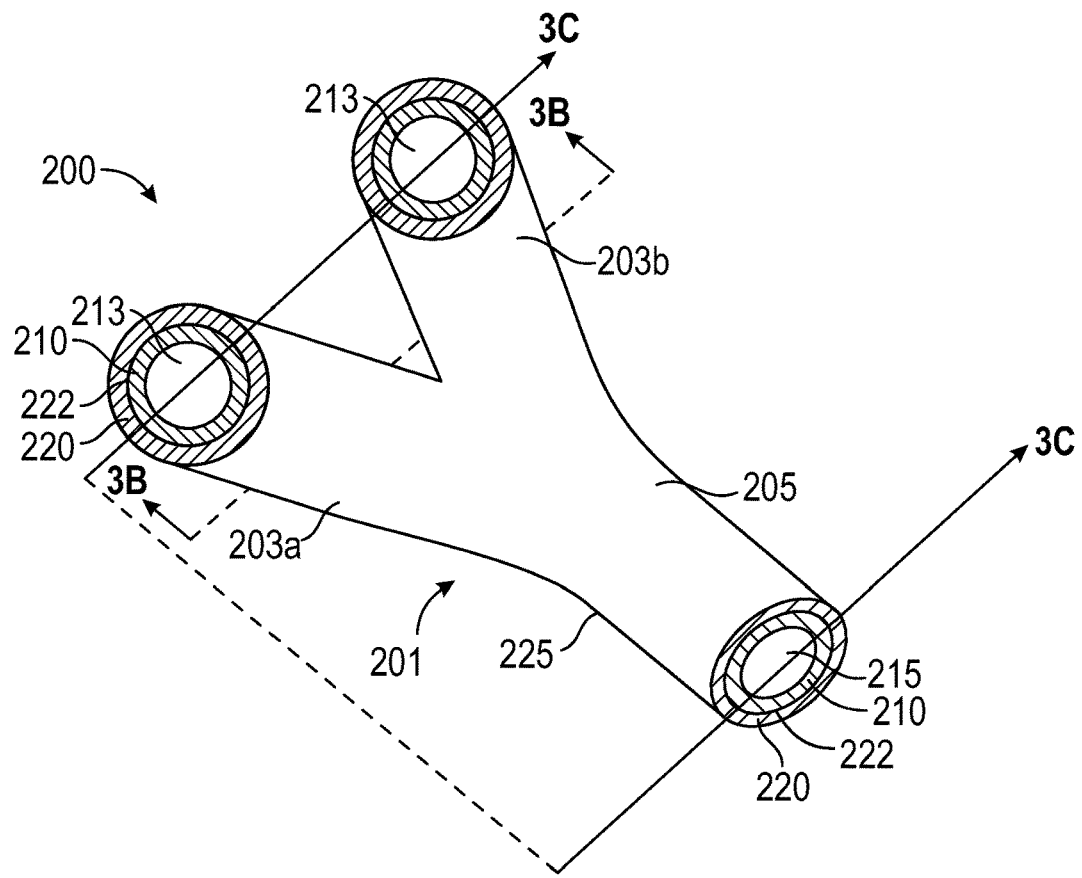
FIG. 3A
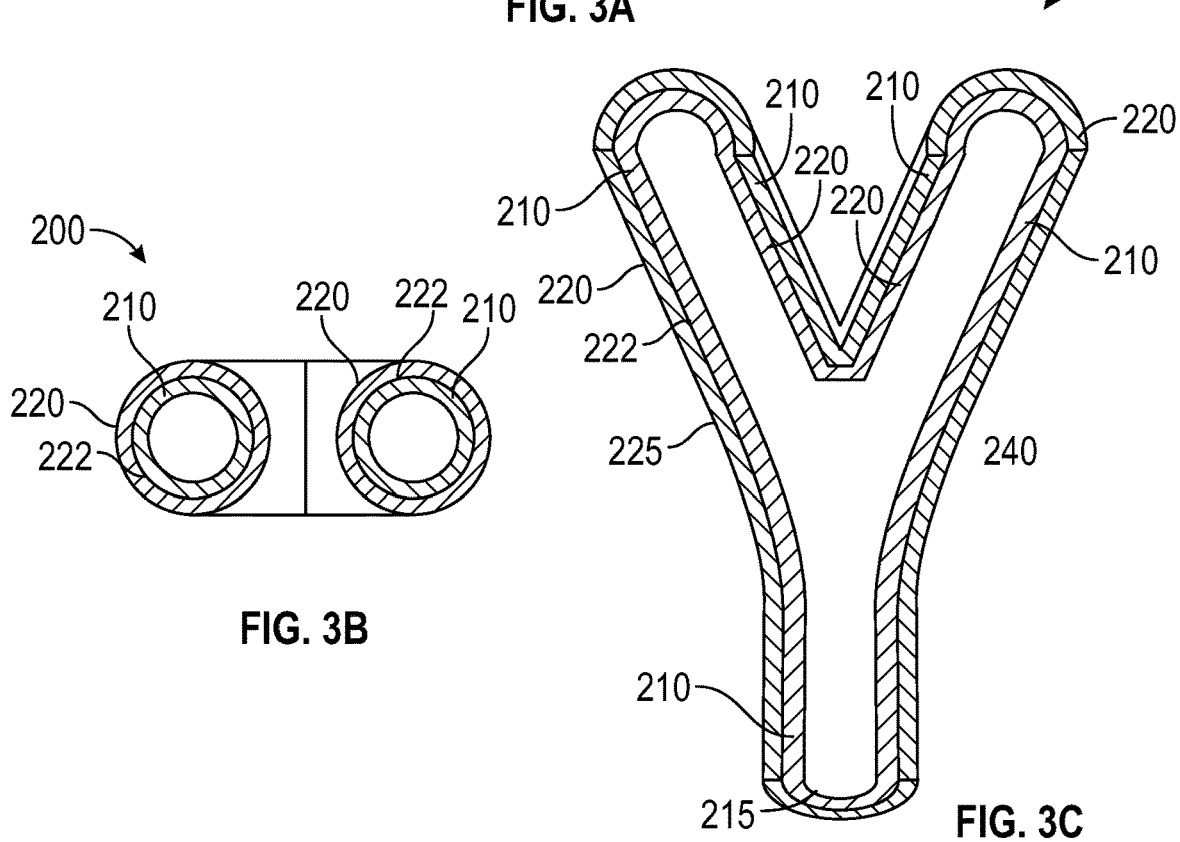
FIG. 3B
FIG. 3C

COMFORTABLE MEDICAL CONNECTORS

TECHNICAL FIELD

The present disclosure relates generally to medical connectors for intravenous (IV) access, and, in particular, to medical connectors having soft, flexible exterior surfaces for reducing discomfort when attached to a patient's skin.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag.

Some medical connectors, for example intravenous (IV) catheters, are used for directing fluid into or withdrawing fluid from a patient. The most common type of IV catheter is an over-the-needle IV catheter. As its name implies, an over-the-needle IV catheter is mounted over an introducer needle having a sharp distal tip. With the distal tip of the introducer needle extending beyond the distal tip of the IV catheter, the assembly is inserted through the patient's skin into a vein. Once placement of the assembly in the vein is verified by flashback of blood in the needle, the needle is withdrawn leaving the IV catheter in place. The proximal end of the IV catheter typically has a hub that is designed to be connectable to an IV fluid supply line after insertion of the IV catheter in a patient.

Although typical IV catheter and introducer needle assemblies generally perform their functions satisfactorily, they do have certain drawbacks. For example, the entire procedure of properly placing an IV catheter into a patient can be cumbersome and awkward and require the use of both hands of the healthcare worker. The IV access/port is often painful, and requires securing of rigid medical accessories to patient's skin.

The description provided in the background section should not be assumed to be prior art merely because it is mentioned in or associated with the background section. The background section may include information that describes one or more aspects of the subject technology.

SUMMARY

In accordance with various embodiment of the present disclosure, a medical connector for minimizing discomfort to a patient, the medical connector may include a substantially rigid inner body, and a flexible outer body having a patient interfacing surface and coupled to at least a portion of the substantially rigid inner body. The patient interfacing surface may include a cushion material. The cushion material may be interposed between the substantially rigid inner body and skin of the patient when the medical connector is attached to the patient.

In accordance with various embodiment of the present disclosure, a method of assembling a connector may include the steps of selecting a rigid inner body material and a flexible outer body material, and overlaying the flexible outer body material along an outer surface of the rigid inner body material.

In accordance with various embodiment of the present disclosure, a medical connector for directing fluid into or withdrawing fluid from a patient may include a multi-compound tubular body formed of alternating layers, including at least one substantially rigid layer having an outer surface, and at least one elastic layer overlaying at least a portion of the outer surface. The outermost elastic layer of the alternating layers may include a patient interfacing surface with cushion material to absorb pressure applied to a patient's body where the medical connector is attached to the patient.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 3A is a perspective view of a medical connector, in accordance with some embodiments of the present disclosure.

FIG. 3B is a cross-sectional view of the medical connector of FIG. 3A, in accordance with some embodiments of the present disclosure.

FIG. 3C is a cross-sectional view of the medical connector of FIG. 3A, in accordance with some embodiments of the present disclosure.

DETAILED DESCRIPTION

Figure 1:
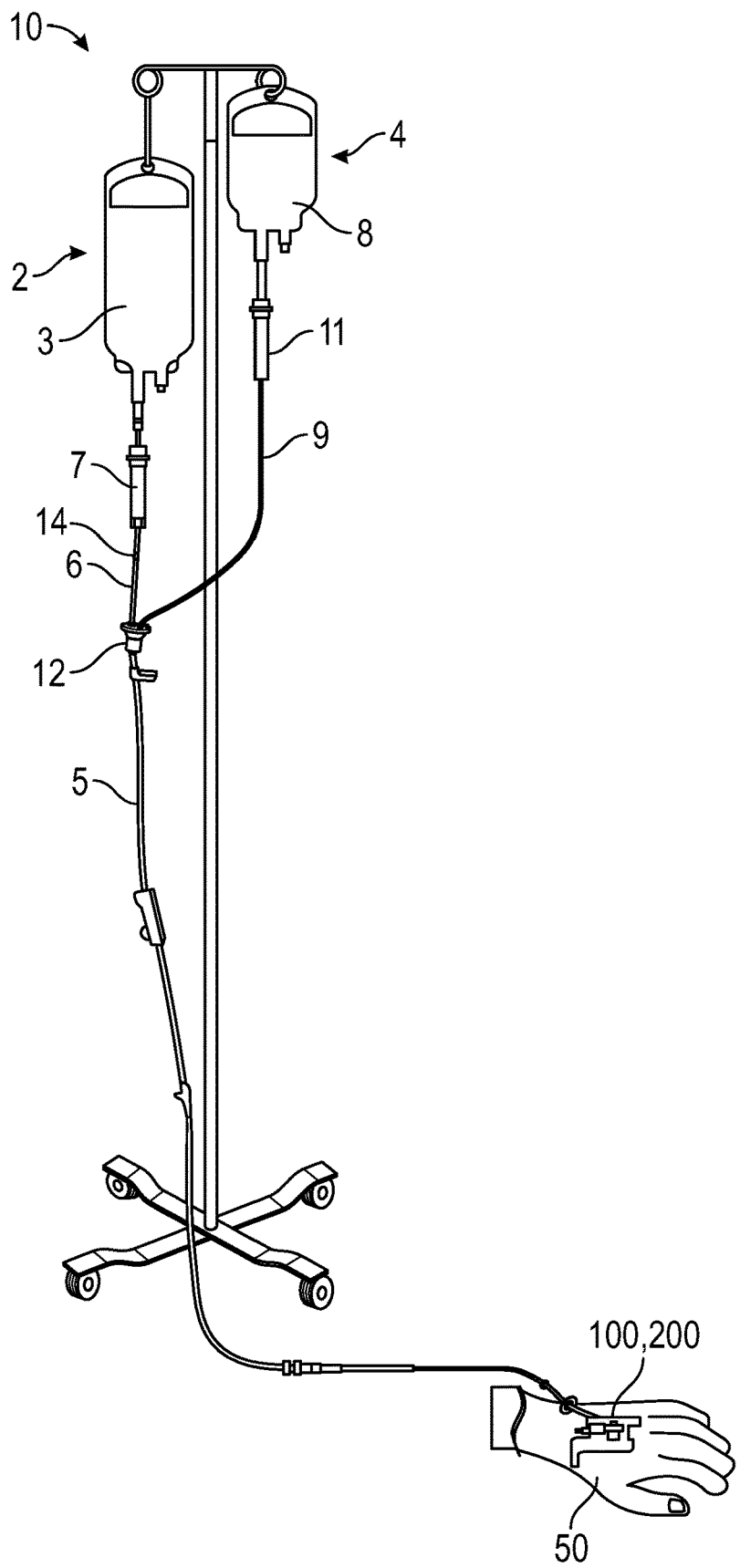
FIG. 1 is a perspective view of an IV set including a medical connector in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure are generally directed to a medical connector for intravenous (IV) access, and, in particular, to medical connectors having soft, flexible exterior surfaces for reducing discomfort when attached to a patient's skin.

As used herein, the terms "medical connector," "connector," "fitting," and any variation thereof refer to any device used to provide a fluid flow path between fluid lines coupled thereto. For example, the medical connector may be or include a bond pocket or other types of connectors. Additionally, the terms "medical connector," "connector," "fitting," and any variation thereof refer to any device used to deliver liquids, solvents, or fluids to or from a patient under medical care. For example, the medical connector may be used for intravenous (IV) delivery of fluids, fluid drainage, oxygen delivery, a combination thereof, and the like to the patient.

In some embodiments, a medical connector may include a substantially rigid inner body and a flexible outer body coupled to at least a portion of the substantially rigid inner body. The flexible outer body may have a patient interfacing surface, which is formed of a cushion material. The cushion material of the flexible outer body may include at least one of silicone, soft plastic, rubber or elastomers. The patient interfacing surface is the outermost surface of the flexible outer body that is in direct contact with the patient's skin when the medical connector is attached to the patient. Accordingly, when the medical connector is attached to the patient the cushion material may be interposed between the substantially rigid inner body and the patient's skin.

In some embodiments, the connector may be formed as multi-compound tubular body having alternating layers of the flexible outer bodies and the rigid inner bodies. For example, the connector may include a plurality of rigid layers and a plurality of flexible or elastic layers, each interposed between adjacent rigid layers. In these embodiments, the outermost flexible or elastic layer may have the patient interfacing surface with cushion material to absorb pressure applied to the patient's body where the connector is attached to the patient.

Currently existing medical connectors incorporate low profiles and special adhesive dressings designed to secure and stabilize the medical connectors to patients. However, these connectors and methods of application are still uncomfortable for the patient and require additional labor time to apply the adhesive dressings. As such, the medical connector may offer further advantages over other connectors commonly attached to patients' bodies. In particular, as previously noted, the medical connector having the flexible outer body with cushion material reduces discomfort to the patient to whom the medical connector is applied.

FIG. 1 is a perspective view of an IV set including a medical connector in accordance with some embodiments of the present disclosure. As illustrated in FIG. 1, an IV set 10 includes the medical connector 100, 200 therein. IV set 10 includes a main fluid system 2 and an auxiliary fluid system 4. An IV pump (not shown) receives fluid from main fluid system 2 and branch or auxiliary fluid system 4 via a supply line 5 and controls and dispenses the fluids therefrom to a patient 50.

Main fluid system 2 may include a main fluid source such as a fluid bag 3, which may include or contain saline solution or other fluid to be administered to the patient. As illustrated, tube 6 may carry flow from a drip chamber 7 to a Y-connector 12. Check valve 14 may be disposed in tube 6 upstream from the Y-connector 12 and enables flow from fluid bag 3 to the IV pump (not illustrated) while preventing reverse flow (backflow) of fluid from auxiliary fluid system 4 toward fluid bag 3.

Auxiliary fluid system 4 includes an auxiliary fluid source such as a fluid bag 8 that may contain drugs or other fluid to be supplied to the patient for treatment. An auxiliary fluid line 9 carries flow from drip chamber 11 to the Y-connector 12.

Various embodiments of the present disclosure relate to medical connectors having soft, flexible exterior surfaces for reducing discomfort when attached to a patient's skin.

Figure 2A:
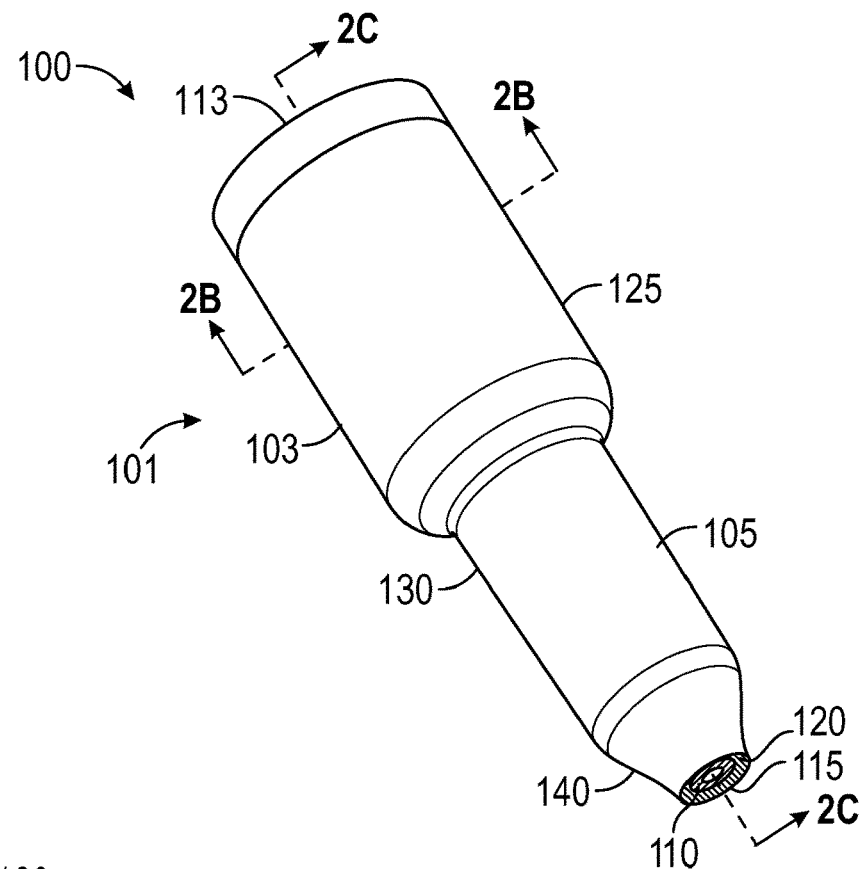
FIG. 2A is a perspective view of a medical connector, in accordance with some embodiments of the present disclosure.
Figure 2B:
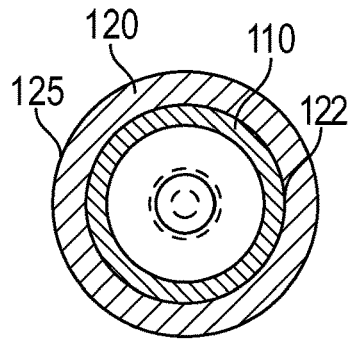
FIG. 2B is a cross-sectional view of the medical connector of FIG. 2A, in accordance with some embodiments of the present disclosure.
Figure 2D:
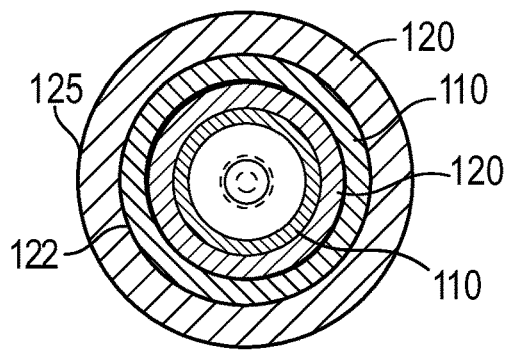
FIG. 2D is a cross-sectional view of a medical connector, in accordance with embodiments of the present disclosure.
Figure 2C:
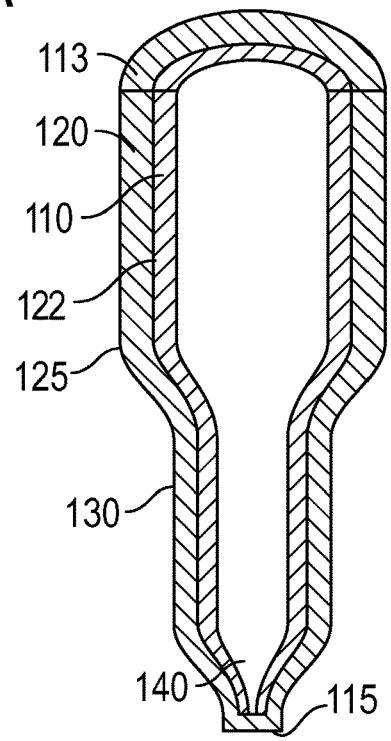
FIG. 2C is a cross-sectional view of the medical connector of FIG. 2A, in accordance with some embodiments of the present disclosure.

FIGS. 2A-2C illustrate an exemplary medical connector 100. The various embodiments of the present disclosure however are not limited to the particular shape illustrated in FIGS. 2A-2C, but can be applied to medical connectors of various shapes and sizes for the purpose of attaching to a patient. FIG. 2A is a perspective view of a medical connector 100, in accordance with some embodiments of the present disclosure. FIG. 2B is a cross-sectional view of the medical connector of FIG. 2A, in accordance with some embodiments of the present disclosure. FIG. 2C is a cross-sectional view of the medical connector of FIG. 2A, in accordance with some embodiments of the present disclosure.

As depicted, the medical connector 100 may include a substantially rigid inner body 110 and a flexible outer body 120 coupled to at least a portion of the substantially rigid inner body 110. In some embodiments, the flexible outer body 120 may include a patient interfacing surface 125, which is formed of a cushion material. A patient interfacing surface as defined herein refers to a surface of the flexible outer body 120 which interfaces directly with the patient's body or skin when attached to the patient. For example, the patient interfacing surface 125 is the outermost surface of the flexible outer body 120, which is in direct contact with the patients skin when the medical connector 100 is attached to the patient. Accordingly, when the medical connector 100 is attached to the patient the cushion material may be interposed between the substantially rigid inner body 110 and the patient's skin.

As such, the medical connector 100 may offer further advantages over other connectors commonly attached to patients' bodies. In particular, as previously noted, the medical connector 100 having the flexible outer body 120 with cushion material reduces discomfort to the patient to whom the medical connector 100 is applied. For example, currently existing medical connectors are made of a rigid material capable of withstanding the day-to-day wear and tear associated with bending and flexing the medical connector 100. Due to the nature of the rigid material, the medical connectors, when pressed against the skin, feel uncomfortable and oftentimes hurt the patient due to the pressure applied.

In some embodiments, the medical connector 100 may have a substantially tubular shape conducive for directing fluid into or withdrawing fluid from the patient.

As illustrated, the medical connector 100 (or simply, connector 100) may include a generally cylindrical body 101 having a "first" or tubing portion 103 and a "second" or needle connection portion 105 axially opposite the tubing portion 103 and connected thereto. The tubing portion 103 may include a tubing port 113 that is sized and shaped or otherwise configured to receive a fluid line (referred to hereafter as "tubing"), as discussed below. Similarly, the needle connection portion 105 may include a needle connection port 115 that is sized and shaped or otherwise configured to receive a needle. As depicted, the body 101 defines an internal longitudinal passageway or bore 140 extending from the tubing port 113 to the needle connection port 115 and fluidly connecting the tubing port 113 and the needle connection port 115 with each other.

The internal bore 140 may be defined by an inner circumferential surface of the rigid inner body 110. In the depicted embodiments, the inner circumferential surface in the tubing portion 103 and the needle connection portion 105 has two non-similar profiles. Specifically, the inner circumferential surface in the tubing portion 103 of the connector 100 may be sized and shaped (or otherwise configured) to receive a tubing. Similarly, the inner circumferential surface in the needle connection portion 105 of the connector 100 may be sized and shaped (or otherwise configured) to receive a needle or other device capable of piercing the patient's skin for directing fluid into or withdrawing fluid from the patient. However, the various embodiments of the present disclosure are not limited to the aforementioned configuration. For example, in some embodiments, a profile of the internal bore defined by the inner circumferential surface may be continuous from the tubing port 113 to the needle connection port 115.

According to various embodiments of the present disclosure the flexible outer body 120 may be a detachable sleeve. To this effect, the flexible outer body 120 may be detachably coupled to the rigid inner body. Advantageously, this configuration would allow for the detachable flexible outer body to be sleeved onto the connector 100 before the connector 100 is attached to the patient and also to be removed and potentially reused on another medical connector as desired. In some embodiments, the flexible outer body 120 may be a coating that is applied to an outer surface 122 of the rigid inner body 110.

In some embodiments, alternatively, the flexible outer body 120 may be co-molded with the substantially rigid inner body 110. For example, a process of making the connector 100 may involve placing the material of the substantially rigid inner body in an injection mold as a base or core component and then the material of the flexible outer body may be injected onto the mold to encapsulate the material of the flexible outer body 120.

In some embodiments, as illustrated in the Figures, the flexible outer body 120 may cover the entire outer surface 122 of the rigid inner body 110. For example, the flexible outer body 120 may be sleeved over, attached to, or co-molded over the entire outer surface 122. However, in other embodiments, the flexible outer body 120 may cover only a portion of the outer surface 122 of the rigid inner body 110. For example, the flexible outer body 120 may cover either all or a portion of only the tubing portion 103, may cover all or only a portion of the needle connection portion 105, or may cover a combination of any of the aforementioned. For example, the flexible outer body 120 may be sleeved over, attached to, or co-molded over either all or only a portion of the tubing portion 103, all or only a portion of the needle connection portion 105, or a combination of any of the aforementioned.

FIG. 3A is a perspective view of a medical connector 200, in accordance with some embodiments of the present disclosure. FIG. 3B is a cross-sectional view of the medical connector 200 of FIG. 3A, in accordance with some embodiments of the present disclosure. FIG. 3C is a cross-sectional view of the medical connector 200 of FIG. 3A, in accordance with some embodiments of the present disclosure. As depicted, the medical connector's 100 may include a substantially rigid inner body 210 and a flexible outer body 220 coupled to at least a portion of the substantially rigid inner body 210. Similar to the connector 100, the flexible outer body 220 of the connector 200 may include a patient interfacing surface 225, which may be formed of a cushion material. As previously described with respect to the connector 100, the patient interfacing surface 225 of the connector 200 is the outermost surface of the flexible outer body 220 that is in direct contact with the patient's skin 50 when the medical connector 200 is attached to the patient. Accordingly, when the medical connector 200 is attached to the patient the cushion material may be interposed between the substantially rigid inner body 210 and the patient's skin 50.

As such, the medical connector 200 may offer further advantages over some connectors commonly attached to patients' bodies. In particular, as previously noted, the medical connector 200 having the flexible outer body 220 with cushion material reduces discomfort to the patient to whom the medical connector 200 is applied. For example, as explained above with respect to other connectors, currently existing medical connectors are made of a rigid material capable of withstanding the day-to-day wear and tear associated with bending and flexing the medical connector. Due to the nature of the rigid material, the medical connectors, when pressed against the skin, feel uncomfortable and oftentimes hurt the patient due to the force applied.

In some embodiments, the medical connector 200 may be in the form of a Y-shaped connector having a tubular form conducive for directing fluid from two sources into or withdrawing fluid from the patient. As illustrated, the medical connector 200 (or simply, connector 200) may include a generally tubular Y-shaped body 101 having a "first" or tubing portion 203 including first and second legs 203a and 203b of the Y-shaped connector. Connector 200 may further include a "second" or needle assembly portion 205 axially opposite the tubing portion 203 and connected thereto. Each of the legs 203a and 203b of the tubing portion 203 may include a tubing port 213 that is sized and shaped or otherwise configured to receive a fluid line (referred to hereafter as "tubing"). In some embodiments one or both of the first and second legs 203a and 203b—instead of including a tubing port—may include a syringe connection port 213 for administration of a medicament from a syringe. Similarly, the needle assembly portion 205 may include a needle assembly connection port 215 that is sized and shaped or otherwise configured to receive a needle assembly. As depicted, each of the legs 203a and 203b and the needle assembly portion 205 defines an internal passageway or bore 240 extending from each of the legs 203a and 203b to the needle assembly connection port 215 and fluidly connecting each of the legs 203a and 203b and the needle assembly connection port 215 with each other.

The internal passageway or bore 240 may be defined by an inner circumferential surface of the rigid inner body 210. In some embodiments, the inner circumferential surface in the tubing portion 203 and the needle assembly connection portion 205 may have similar tubular profiles. In other embodiments, the inner circumferential surface in the tubing portion 203 and the needle assembly connection portion 205 may have non-similar tubular profiles. Specifically, the inner circumferential surface in the legs 203a and 203b may be sized and shaped (or otherwise configured) to receive a tubing or a syringe. Similarly, the inner circumferential surface in the needle assembly connection portion 205 may be sized and shaped (or otherwise configured) to receive a needle assembly, catheter assembly, or other device or assembly capable of piercing the patient's skin for directing fluid into or withdrawing fluid from the patient. However, the various embodiments of the present disclosure are not limited to the aforementioned configuration.

According to various embodiments of the present disclosure the flexible outer body 220 may be a detachable sleeve. To this effect, similar to some embodiments of the connector 100, the flexible outer body 220 may be detachably coupled to the rigid inner body 210. Advantageously, this configuration would allow for the detachable flexible outer body 220 to be sleeved onto the rigid inner body 210 before the connector 200 is attached to the patient, and also to be removed and potentially reused on another medical connector as desired. In some embodiments, the flexible outer body 220 may be a coating that is applied to an outer surface 222 of the rigid inner body 210.

In some embodiments, alternatively, the flexible outer body 220 may be co-molded with the substantially rigid inner body 210. For example, a process of making the connector 200 may involve placing the material of the substantially rigid inner body 210 in an injection mold as a base or core component and then the material of the flexible outer body 220 may be injected onto the mold to encapsulate the material of the flexible outer body 220.

In some embodiments, as described before with respect to the connector 100, the flexible outer body 220 may cover the entire outer surface 222 of the rigid inner body 210. For example, the flexible outer body 220 may be sleeved over, attached to, or co-molded over the entire outer surface 222. However, in other embodiments, the flexible outer body 220 may cover only a portion of the outer surface 222 of the rigid inner body 210. For example, the flexible outer body 220 may cover either all or a portion of only legs 203*a* and 203*b* of the tubing portion 203, may cover all or only a portion of the needle assembly connection portion 105, or may cover a combination of any of the aforementioned. For example, the flexible outer body 220 may be sleeved over, attached to, or co-molded over either all or only a portion of legs 203*a* and 203*b* of the tubing portion 203, all or only a portion of the needle assembly connection portion 205, or a combination of any of the aforementioned.

In some embodiments, the connectors 100, 200 may be formed as multi-compound tubular bodies having alternating layers of the flexible outer bodies 120, 220 and the rigid inner bodies 110, 210. For example, the connector 100 may include a plurality of rigid layers 110 and a plurality of flexible or elastic layers 120, each interposed between adjacent rigid layers 110. In these embodiments, the outermost flexible or elastic layer 120 may have the patient interfacing surface 125 with cushion material to absorb pressure applied to the patient's body where the connector 100 is attached to the patient. In some embodiments, the outermost flexible or elastic layer 120 of the alternating layers 110 and 120 may cover an entirety of the outer surface 122 of the adjacent rigid layer 110.

In some embodiments, the outermost flexible or elastic layer 120 of the alternating layers 110 and 120 may cover only a portion of the outer surface 122 of the adjacent rigid layer 110. Similarly, the connector 200 may include a plurality of rigid layers 210 and a plurality of flexible or elastic layers 220, each interposed between adjacent rigid layers 210. In these embodiments, the outermost flexible or elastic layer 220 may have the patient interfacing surface 225 with cushion material to absorb pressure applied to the patient's body where the connector 100 is attached to the patient. In some embodiments, the outermost elastic layer 220 of the alternating layers 210 and 220 may cover an entirety of the outer surface 222 of the adjacent rigid layer 210. In other embodiments, the outermost elastic layer 220 of the alternating layers 210 and 220 may cover only a portion of the outer surface 222 of the adjacent rigid layer 210.

For example, in some embodiments, the flexible or elastic layer 120, 220 may extend around only the tube or syringe connecting portions 103, 203*a*, 203*b*, and in some embodiments, the flexible or elastic layer 120, 220 may extend around only the needle assembly portion 105, 205. In these embodiments, cushion material may be placed in locations on the connector 100 that are found to be most beneficial without need to cover the entire connector 100. In some embodiments, the cushion material of the flexible or elastic layer 120 may be placed in a transition area between the tube or syringe connecting portions 103, 203*a*, 203*b* and the corresponding needle assembly portion 105, 205.

In some embodiments, the flexible outer body 120, 220 may be made of, but not limited to, at least one of silicone, soft plastic, rubber or elastomers. The substantially rigid inner body 110, 210 may be made of, but not limited to, at least one of plastic, ceramic, metal, or a composite thereof. Accordingly, the flexible or elastic outer body 120, 220 may act as a cushion/padding of the respective connectors 100, 200 to reduce the discomfort associated with pressure applied onto patients' skin by conventional connectors.

In some embodiments, the flexible outer body 120, 220 may have a color different than that of the substantially rigid inner body 110, 210.

According to various aspects of the present disclosure a method of assembling a connector 100, 200 may include selecting a rigid inner body material and a flexible outer body material and overlaying the flexible outer body material along an outer surface of the rigid inner body material. In some embodiments, the step of overlaying the flexible outer body material along the outer surface of the rigid inner body material may include co-molding the flexible outer body material with the rigid inner body material to form a tubular rigid inner body 110, 210 overlaid at least in part with a flexible outer body 120, 220. In some embodiments, the step of overlaying the flexible outer body material along the outer surface of the rigid inner body material may include forming the rigid inner body material into a tubular rigid inner body 110, 210 and sleeving the flexible outer body material over at least a portion of the outer surface of the rigid inner body.

In some embodiments, the step of selecting a rigid inner body material and a flexible outer body material may include selecting a plurality of layers of the rigid inner body material and a plurality of layers of the flexible outer body material. The step of overlaying the flexible outer body material along an outer surface of the rigid inner body material may include forming a multi-compound tubular body having alternating layers of the rigid inner body material and the flexible outer body material. In these embodiments, the outermost layer of the flexible outer body material may have a patient interfacing surface with cushion material to absorb pressure.

The patient interfacing medical connectors 100, 200 of the various embodiments described herein retain the capability to withstand the day-to-day rigors associated with bending and flexing by incorporating the rigid material as an inner or base layer. Contrary to existing connectors, the medical connectors 100, 200 of the various embodiments described herein have the added advantage of having a soft, flexible material overlaying the rigid inner body. This soft flexible material acts as a cushion or buffer to protect the patient's skin from being directly pressed against by rigid connector material. As such, the soft cushion/buffer minimizes discomfort to the patient which would otherwise be experienced in light of the rigid material connectors are traditionally made from.

In contrast, conventional medical connectors have rigid outer surfaces and require a precise method of taping the connector to the patient's skin in an effort to ease discomfort while still providing a secure attachment. This is disadvantageous as the method of application may be complex and require additional labor time. Additionally, because conventional connectors have no outer cushion layer to protect the patient's skin, the patient will still feel discomfort resulting from pressure of the attached rigid connector.

Further, conventional connectors often have a mechanical structure designed to accommodate specific type of mating connectors, which limits the variety or range of mating connectors they can be used with. In contrast, since the connectors 100, 200 are not limited to any specific form of structure other than a flexible cushion layer or body overlaying a rigid connector base layer or body, the connectors of the present disclosure can accommodate a wide range of mating connectors. The connectors of the present disclosure may be used in bond pocket or in rigid to rigid mating connections. Furthermore, conventional medical connectors often require a perfected mating surface in order to achieve a secure connection with a mating connector or other mating surface. In contrast, the flexible cushion layer or body of the connectors of the present disclosure allow for imperfection in mating surfaces while still providing a secure connection.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A medical connector for minimizing discomfort to a patient, the medical connector comprising:
   a plurality of substantially rigid layers and a plurality of elastic layers interposed between adjacent layers of the plurality of substantially rigid layers, wherein an innermost layer of the plurality of substantially rigid layers forms a tubing port and a connection port; and
   an outermost layer of the plurality of elastic layers forms a patient interfacing surface extending over an entire outer surface of the adjacent layer of the plurality of substantially rigid layers, from the tubing port to the connection port.

2. The medical connector of claim 1, wherein the plurality of elastic layers comprise at least one of silicone, soft plastic, rubber or elastomers.

3. The medical connector of claim 1, wherein the outermost layer of the plurality of elastic layers comprises a detachable sleeve.

4. The medical connector of claim 1, wherein the plurality of elastic layers comprise at least one of a coating, a co-molded body, or an attached layer.

5. The medical connector of claim 1, wherein the plurality of elastic layers comprise a color different than that of the plurality of substantially rigid layers.

6. The medical connector of claim 1, wherein the plurality of substantially rigid layers comprise at least one of plastic, ceramic, or metal.

7. The medical connector of claim 1, wherein the innermost layer of the plurality of substantially rigid layers comprises a longitudinal passageway extending from the tubing port to the connection port.

8. A method of providing a connector for minimizing discomfort to a patient, the method comprising the steps of:
   providing a plurality of rigid layers and a plurality of elastic layers interposed between adjacent layers of the plurality of rigid layers, wherein an innermost layer of the plurality of rigid layers forms a tubing port and a connection port; and
   providing an outermost layer of the plurality of elastic layers overlaying an entire outer surface of the adjacent layer of the plurality of rigid layers from the tubing port to the connection port.

9. The method of claim 8, wherein:
   providing the outermost layer of the plurality of elastic layers comprises co-molding the outermost layer of the plurality of elastic layers with the adjacent layer of the plurality of rigid layers.

10. The method of claim 8, wherein providing the outermost layer of the plurality of elastic layers comprises forming a layer of the plurality of rigid layers into a tubular rigid inner body and sleeving a layer of the plurality of elastic layers over at least a portion of the outer surface of the layer of the plurality of rigid layers.

11. The method of claim 8, wherein the plurality of elastic layers comprise at least one of silicone, soft plastic, rubber, or elastomers.

12. The method of claim 8, wherein the plurality of rigid layers comprise at least one of plastic, ceramic, or metal.

13. A medical connector for directing fluid into or withdrawing fluid from a patient, the medical connector comprising:
   a multi-compound tubular body comprising a tubing port, a connection port, a plurality of substantially rigid layers, and a plurality of elastic layers interposed between adjacent layers of the plurality of substantially rigid layers;
   wherein a layer of the plurality of elastic layers forms an outer surface of the multi-compound tubular body extending from the tubing port to the connection port and configured to absorb pressure applied to a patient's body where the medical connector is attached to the patient.

14. The medical connector of claim 13, wherein the outer surface of the multi-compound tubular body comprises a detachable sleeve.

15. The medical connector of claim 13, wherein at least one layer of the plurality of elastic layers is co-molded with the at least one layer of the plurality of substantially rigid layers.

16. The medical connector of claim 13, wherein at least one layer of the plurality of elastic layers comprises at least one of silicone, soft plastic, rubber, or elastomers.

17. The medical connector of claim 13, wherein at least one layer of the substantially rigid layers comprises at least one of plastic, ceramic, or metal.

18. The medical connector of claim 13, wherein an innermost layer of the plurality of substantially rigid layers comprises a longitudinal passageway extending from the tubing port to the connection port.

* * * * *